(12) United States Patent
Hof et al.

(10) Patent No.: US 8,787,641 B2
(45) Date of Patent: Jul. 22, 2014

(54) METHOD AND APPARATUS FOR QUANTITATIVE ANALYSIS OF A TREE OF RECURSIVELY SPLITTING TUBULAR ORGANS

(75) Inventors: Jacobus Adrianus Engelbertus Johannes Hof, Eindhoven (NL); Sjoerd Diepen, Kuala Lumpur (MY); Ron Hubertus Schormans, Heerlen (NL)

(73) Assignee: Pie Medical Imaging B.V., Maastricht (NL)

(*) Notice: Subject to any disclaimer, the term of this patent is extended or adjusted under 35 U.S.C. 154(b) by 0 days.

(21) Appl. No.: 13/819,891

(22) PCT Filed: Sep. 2, 2010

(86) PCT No.: PCT/EP2010/062883
§ 371 (c)(1),
(2), (4) Date: Feb. 28, 2013

(87) PCT Pub. No.: WO2012/012190
PCT Pub. Date: Mar. 8, 2012

(65) Prior Publication Data
US 2013/0158970 A1 Jun. 20, 2013

(51) Int. Cl.
*G06K 9/00* (2006.01)
(52) U.S. Cl.
USPC .......................................................... 382/128
(58) Field of Classification Search
None
See application file for complete search history.

(56) References Cited

U.S. PATENT DOCUMENTS

| | | | |
|---|---|---|---|
| 8,155,411 B2* | 4/2012 | Hof et al. ...................... | 382/128 |
| 2007/0116342 A1* | 5/2007 | Zarkh et al. ................... | 382/130 |
| 2009/0060298 A1* | 3/2009 | Weijers et al. ................ | 382/128 |
| 2010/0021025 A1* | 1/2010 | Hof et al. ...................... | 382/128 |

OTHER PUBLICATIONS

Polygon Mesh, Wikipedi: the free encyclopedia, Aug. 22, 2009.*
Arbab-Zadeh, A., et al. "Quantification of lumen stenoses with known dimensions by conventional angiography and computed tomography: implications of using conventional angiography as gold standard." Heart 96.17, Sep. 1, 2010: 1358-1363.*

(Continued)

*Primary Examiner* — Stephen R Koziol
*Assistant Examiner* — Raphael Schwartz
(74) *Attorney, Agent, or Firm* — Gordon & Jacobson, PC (57) ABSTRACT

Method for quantitative analysis of a tree or part of a tree of recursively splitting tubular organs, the method comprising the following steps: —providing a 3D model of said tree or part of said tree, such 3D model giving a representation of the surface of the lumen wall of the tubular organs forming the tree or part of the tree; —defining the 3D centerlines of said tree or part of the tree; —identifying the branches of the tree; —identifying N-furcations of the tree or part of the tree, an N-furcation being a part of the tree where a proximal tubular organ branches into two or more distal tubular organs, further comprising the step of: —dividing, independently from the modality used for obtaining the 3D model, each branch in one or more regions, such regions being of two different types, named single vessel region and splitting region, different cross-section surfaces being defined in such regions, wherein the splitting regions can exist at the proximal side of a branch as well as at the distal side of said branch and each N-furcation comprises the distal splitting region of a branch and the proximal splitting regions of the N branches directly distal to said branch. A corresponding apparatus and computer program are also disclosed.

25 Claims, 6 Drawing Sheets

(56) References Cited

OTHER PUBLICATIONS

"Geometric Variability of the Abdominal Aorta and Its Major Peripheral Branches", Padraig M. OA Flynn et al, Annals of Biomedical Engineering, Kluwer Academic Publishers-Plenum Publishers, NE, vol. 38, No. 3, Jan. 20, 2010, pp. 824-840.

"A Parametric Model for Studies of Flow in Arterial Bifurcations", Hasballah Zakaria et al, Annals of Biomedical Engineering, Kluwer Academic Publishers-Plenum Publishers, NE, vol. 36. No. 9, Jul. 16, 2008, pp. 1515-1530.

* cited by examiner

METHOD AND APPARATUS FOR QUANTITATIVE ANALYSIS OF A TREE OF RECURSIVELY SPLITTING TUBULAR ORGANS

CROSS-REFERENCE TO RELATED APPLICATION

This application claims priority from PCT/EP/2010/062883 filed on Sep. 2, 2010 which is hereby incorporated by reference in its entirety.

FIELD OF THE INVENTION

The present invention relates to a method and apparatus for a generic and accurate 3D quantitative vascular analysis of a tree of recursively splitting tubular organs.

STATE OF THE ART

Vascular image analysis refers to the process of investigating arteries. In clinical practice it is particularly used to determine the severity of any narrowing that may exist, such as by finding obstructed arteries. Quantitative Coronary analysis (QCA) of single arteries has become a standard for objective quantitative assessment of the severity of the obstruction. It is also widely used in clinical trail studies. A clinical trail aims to collect data about the efficacy of a treatment.

Quantitative analysis of an N-furcation, i.e. the splitting of a proximal tubular organ into two or more distal tubular organs, has become of increasing clinical interest as obstructions not only arise in single tubular organs, but also in regions where they split up. Quantitative analysis methods have been developed to enable the assessment of the severity of an obstruction at a bifurcation.

Most present developments in the field focus on the reconstruction of tubular organs in 3D. This can be achieved by creating a 3D model of the tubular organs based on some imaging modality. Such modalities include, but are not necessarily limited to, X-ray, MR, CT, and ultrasound.

Having a 3D reconstruction, it would be preferable to also have a corresponding quantitative analysis in 3D. However, developments, particularly in the field of X-ray angiography, have been made only towards combining or fusing the quantitative analysis data from multiple 2D representations.

This has drawbacks as not only may lead to masking of information that is present and may only be observed in 3D, but also renders the analysis dependent on the imaging modalities used for obtaining the 3D dataset. This results in quantitative vascular analysis apparatus that cannot be used for multiple imaging modalities, although that would be highly desirable. In fact, enabling inter-modality quantitative analysis result comparisons and a uniform way of measurement among different modalities would certainly improve diagnostic tools at disposal of the medical community, particularly if such a quantitative analysis is performed not only on single tubular organs or bifurcations, but on the whole vessel tree.

Currently no piece of prior art has solved the above limitations.

International Patent Application WO2005/031635 describes the 3D reconstruction of only a single vessel based on multiple X-ray projections and analysis of the vessel. The analysis is based on measurements in 2D images used for the 3D reconstruction and thus does not represent a full 3D analysis of the 3D model. A model of the healthy vessel is provided as visual feedback.

In U.S. Pat. No. 7,321,677 it is said that a 3D quantitative analysis is performed. However, stenosis related parameters can only be computed for a single artery which can be detected by analysis of 2D angiographic images, which were used to construct a 3D model. Based on this model, two orthogonal perspectives are determined and suggested. After acquiring images based on the suggested perspectives, which may imply an extra step of image acquisition if these perspectives were not already present, a 3D reconstruction of the artery of interest can be recreated. Furthermore the method according to this prior art document deals with single arteries, i.e not trees including N-furcations. Hence also this document fails to disclose a full 3D analysis of a tree of recursively splitting organs. No healthy model for visual feedback is also mentioned.

United States Patent Application published with number US2009/0060298 describes a method to perform a quantitative bifurcation analysis either for a single bifurcation or for detecting a multiple-vessel-tree bifurcation combination, but is limited to 2D.

United States Patent Application published with number US2010/021025 is limited to X-ray. Also, for bifurcation analysis it provides a solution that combines multiple 2D quantitative bifurcation analyses instead of providing a true 3D solution. This poses a problem in case there is a lot of overlap near the bifurcation. One could try to search for more suitable image projections. However, certainly in case a vascular tree will be analysed, this is undesirable with respect to the patient in terms of X-ray exposure and contrast agent usage.

SUMMARY OF THE INVENTION

It is therefore an object of the invention to extend prior art and to provide a more accurate and reproducible method and system for 3D quantitative analysis of a tree of recursively splitting tubular organs.

The invention achieves the aim with a method for quantitative analysis of a tree or part of a tree of recursively splitting tubular organs, the method comprising the following steps:
  providing a 3D model of said tree or part of said tree, such 3D model giving a representation of the surface of the lumen wall of the tubular organs forming the tree or part of the tree;
  defining the 3D centrelines of said tree or part of the tree;
  identifying the branches of the tree;
  identifying N-furcations of the tree or part of the tree, an N-furcation being a part of the tree where a proximal tubular organ branches into N distal tubular organs with N≥2,
further comprising the step of
  dividing, independently from the modality used for obtaining the 3D model, each branch in one or more regions, such regions being of two different types, named single vessel region and splitting region, different cross-section surfaces being defined in such regions,
wherein
  said splitting regions can exist at the proximal side of a branch as well as at the distal side of said branch; and
  each N-furcation comprises the distal splitting region of a branch and the proximal splitting regions of the N branches directly distal to said branch.

The idea at the basis of the invention is the identification of zones in the tree having common characteristics. This is done by defining, in any branch of the tree, regions characterized by different type of cross-sections and identifying N-furcations as single objects formed by the combination of regions of different branches having common characteristics. All that independently from the modality used for obtaining the 3D model.

Treating of N-furcations as single objects is particularly advantageous, as it enables catching characteristic aspects which differ significantly from single vessel regions. Such characteristic aspects would not be covered fully if one, for example, analysed merged branches, i.e. branches constructed by interpolation, from proximal to distal in each of the splitting directions.

Being the analysis a full 3D analysis, cross sections are complex 3D surfaces which do not necessarily belong to a cut plane, however there are zones sufficiently far from a N-furcation where such cross sections can be considered straight. Typically straight surfaces belong to a cut plane, particularly a cut plane perpendicular to the local branch orientation. These zones are called in the present invention "single vessel regions". The remaining zones are, instead, called "splitting regions" as they are only present in regions where a branch splits up in N-furcations. The cross-sections of the splitting regions are typically curved surfaces. Particularly the cross-sections of the splitting regions are curved in order to take into account perpendicularity to the flow of a fluid perfusing the tree or part of the tree in each of the splitting directions. Each N-furcation of the tree is formed by splitting regions of consecutive branches.

A part of the invention is the definition of the boundary surfaces between a splitting region and a single vessel region for each branch. According to an advantageous improvement, such boundary surfaces are cross-sections of the single-vessel-region type.

According to an embodiment, the proximal boundary surface of a single vessel region of a branch is computed by iteratively finding the most proximal straight cross-section over the centreline of said branch, whose contour is entirely part of said branch, falls within a single plane containing the corresponding position on said centreline and is oriented such that it has minimal area at said position.

Analogously, the distal boundary surface of a single vessel region of a branch is computed by iteratively finding the most distal straight cross-section over the centreline of said branch, whose contour is entirely part of said branch, falls within a single plane containing the corresponding position on said centreline and is oriented such that it has minimal area at said position.

Advantageously the finding of the orientation of said cross-section such that the area of said cross-section is minimal can be achieved with the following steps:
  defining the orientation in a spherical domain, thereby ignoring the radius dimension;
  limiting said domain to one cycle in each of both remaining angular dimensions;
  splitting up said domain in rectangular subdomains and for each subdomain calculating the cross-sectional area for the orientation specified by the centrevalue of said subdomain;
  replacing said domain by one of said subdomains, more specifically the subdomain for which the calculation of said cross-sectional area for said centrevalue resulted in minimal area;
  repeating calculation of said centrevalue and replacing of said subdomain until the domain size reaches a pre-defined threshold.

These steps are particularly advantageous, as, given that care is taken with respect to local minima, they result in a fast numerical solution to the minimization problem.

As a part of the quantitative analysis, the cross-sectional area at each position of the centreline of the 3D model may be determined by computing the area of the cross section surfaces as defined for single vessel regions and splitting regions.

According to an embodiment, for proximal splitting regions, the area of the curved surface cross-sections may be calculated by:
  computing the levelset between the circumferential contour bounding the branch at its proximal side and the contour surrounding the distal boundary surface to determine corresponding iso-contours which circumferentially contour the lumen;
  linking the iso-contours to the centreline points based on the iso-value that corresponds to the centreline point located at the distance where the fraction of the total centreline distance between the first and last iso-contours equals the iso-value having same fraction between the levels of said first and last iso-contours;
  computing for each centreline point the surface of the cross-section bounded by the linked isocontour of said centreline point, said surface being curved and having the minimum energy;
  computing the area of said surface for each said centreline points.

For distal splitting regions, the area of the curved surface cross-sections can be calculated by:
  computing the levelset between the contour surrounding the proximal boundary surface and the circumferential contour bounding the branch at its distal side;
  linking the iso-contours to the centreline points of the centreline having the longest route between said contours based on the iso-value that corresponds to the centreline point located at the distance where the fraction of the total centreline distance between the first and last iso-contours equals the iso-value having same fraction between the levels of said first and last iso-contours;
  linking the iso-contours to centreline points of the remaining centrelines after a centreline split-off point using already present links, based on the fraction of the distance of a centreline point to said split-off point compared to the total distance measured between the split-off of centrelines to the end of the branch, where a said already present link has an equal fraction of distance between said split-off and the end of the branch;
  computing for each centreline point the surface of the cross-section bounded by the linked iso-contour of said centreline point, said surface being curved and having the minimum energy;
  computing the area of said surface for each said centreline point.

For single vessel regions, the area of the straight cross-sections may be calculated by:
  computing the levelset between the contour surrounding the proximal boundary surface and the contour surrounding the distal boundary surface;
  linking each centreline point to cross-sectional contours having minimum standard deviation in levelset value whereby said contours surround a cross-section containing said centreline point;
  computing the area of said cross-section for each said centreline point.

These steps are particularly advantageous as they prevent area overestimation, particularly of obstructions, as it will be explained in detail hereinafter.

The minimal energy surface of a circumferential contour within a splitting region may be advantageously calculated iteratively by:

defining straight lines from each contour vertex of said circumferential contour to the centre of gravity of said circumferential contour and dividing said lines in n rings containing m samples wherein the vertices of said circumferential contour are the samples of the first ring and each inner ring contains less samples than its outer neighbour and, besides the first two, two successive rings do not sample same rays;

defining a surface mesh between ring points;

computing total area of said surface mesh;

fixing said samples of said first ring and keep moving each other sample in mean neighbour direction until change in mesh area and/or movement of the samples is less than a predefined threshold.

Quantitative analysis results are typically presented with reference to the tree, said results including length, area, diameter, angles between branches, curvature. According to an improvement the method also comprises the step of determining a circularity graph indicating healthiness over the tubular organ that can be found by dividing the radius of a maximum inscribed sphere by the radius of the minimum bounding circle of a cross-section at each centreline position within a single vessel region.

According to an embodiment, a healthy reconstruction is provided and/or computed, such healthy reconstruction being a 3D model giving a representation of the surface of the healthy lumen wall of the tubular organs forming the tree or part of the tree. This is useful for providing a reference to measurements. For example the extension of an obstruction is usually indicated as a percentage of narrowing with reference to the considered healthy vessel lumen. Quantitative analysis results are, in fact, preferably presented with reference to the healthy tree reconstruction in relation to the tree reconstruction.

To such extent, the method according to the invention preferably comprises the steps of:

creating healthy reconstruction or reconstructions of the singular tubular organs as contour model;

creating healthy reconstruction or reconstructions of the N-furcations, each of said healthy reconstruction or reconstructions being divided in N parts with each of said parts describing minimum lumen curvature going from proximal to distal and combining said parts as contour model;

combining all reconstructed singular tubular organs and N-furcations into one contour model;

creating a healthy model surface mesh from said contour model forming the healthy tubular organs forming the tree or part of the tree;

defining 3D centrelines for the healthy tubular organs forming the tree or part of the tree;

defining N-furcations in the healthy tubular organs forming the tree or part of the tree;

linking centrelines of the healthy model tree to the centrelines of the tree;

creating cross-sections and computing area curves for N-furcations;

creating cross-sections for single tubular organs;

computing area curves for the single tubular organs based on the computed reference.

The cross-sections and/or area curves are preferably created and/or computed and/or defined by applying one or more steps as disclosed above with reference to the 3D model of the real tree while the linking of the centrelines is typically based on the healthy model tree having the same topology as the real tree. Using the same calculations/definitions has the advantage of improving the registration and/or fusion between the two models for more accurate quantitative measurements. Different ways of calculations/definitions can also be considered particularly for single vessels.

According to an improvement, healthy splitting regions are reconstructed with a model that minimizes the curvature of the lumen wall going from the start of an N-furcation to each of the distal ends of that N-furcation. Said 3D model is typically assumed healthy except for one or more obstructed parts of said 3D model, whereby each of said obstructed parts reflects a 3D model of a subtree of said tree and said obstructed parts are automatically derived based upon one or more automatically computed or user supplied lesion positions.

Besides obtaining obstruction analysis related measurements, the healthy model is advantageously used to provide visual feedback of the plaque shape and location.

In some configurations, one or more subtrees of the tubular organs originating from any of the N-furcations of the tree may also be ignored.

The healthy reconstruction and related processing can obviously be provided and/or computed after or even in parallel with the real tree processing. In general all the steps of the method according to the invention are not to be considered strictly in the order presented, but can be equally performed in any other meaningful sequence.

The method of the invention is typically performed by a data processing system with access to the volumetric image data of a tree or part of a tree of recursively splitting organs.

According to another aspect, the invention also relates to a corresponding apparatus for quantitative analysis of a tree or part of a tree of recursively splitting tubular organs. The apparatus comprises means for receiving and/or computing a 3D model of the tree or part of the tree, such 3D model giving a representation of the surface of the lumen wall of the tubular organs forming the tree or part of the tree, and processing means programmed for performing the method according to the invention. Advantageously, such an apparatus could be the same machine used for acquiring and/or reconstructing the image data, such as CT, MRI, Ultrasound or X-ray machines. The processing means could be a processor or processors dedicated to perform the method according to the invention or, in a particularly advantageous configuration, the same, or part of the same, processing means that subtends the main image acquisition functionalities of the machine thus obtaining a very compact and powerful apparatus.

The invention also relates to a computer product directly loadable into the memory of a computer and comprising software code portions for performing the method as disclosed above when the product is run on a computer.

The invention provides a true 3D analysis of an entire vascular tree or parts of it and is suitable to deliver the corresponding reference curves and healthy reconstruction of an entire vascular tree or parts of it. The method elaborates on the notion that the bifurcation is handled as a single object. The invention includes the measurement of several medical features that are clinically relevant. These features include amongst others: cross-sectional area and diameter, diameter stenosis, obstruction percentage, plaque volume, obstruction extent, and position of largest obstruction (i.e. lesion position).

Furthermore, the invention is suitable for the analysis of trifurcations, or in general N-furcations. Also the invention provides a way to ignore one or more of splitting tubular organs in an N-furcation when these are considered irrelevant for analysis. The tree can consist of a number of recursively splitting tubular organs, as indicated, for example, in FIG. 2, or just one splitting tubular organ such as the one shown in FIG. 11. In the latter case when ignoring two splitting tubular organs, a single tubular organ remains.

Further improvements of the invention will form the subject of the dependent claims.

BRIEF DESCRIPTION OF THE DRAWINGS

The characteristics of the invention and the advantages derived therefrom will be more apparent from the following description of non-limiting embodiments, illustrated in the annexed drawings, in which.

For convenience, FIG. 2, 3, 4, 6, 7, 8 are 2D representations of the 3D situation described in the embodiment.

DETAILED DESCRIPTION OF A PREFERRED EMBODIMENT

For purposes of description herein, the following terms are defined as follows:

"proximal" is a term meaning the side of a vessel or tube or tubular organ from which a fluid comes; for example the proximal side of the aorta is the side of the aorta closest to the heart;

"distal" is a term meaning the side of a vessel or tube or tubular organ where the fluid flows to; for example the distal side of the aorta is the side of the aorta furthest from the heart;

"lumen" is a term meaning the interior of a vessel or tube or tubular organ through which a fluid flows or the external boundary of the vessel wall, or any position in-between;

"healthy" is a term meaning the estimated tubular organ dimension as if it were without obstruction or dilation.

Figure 1:
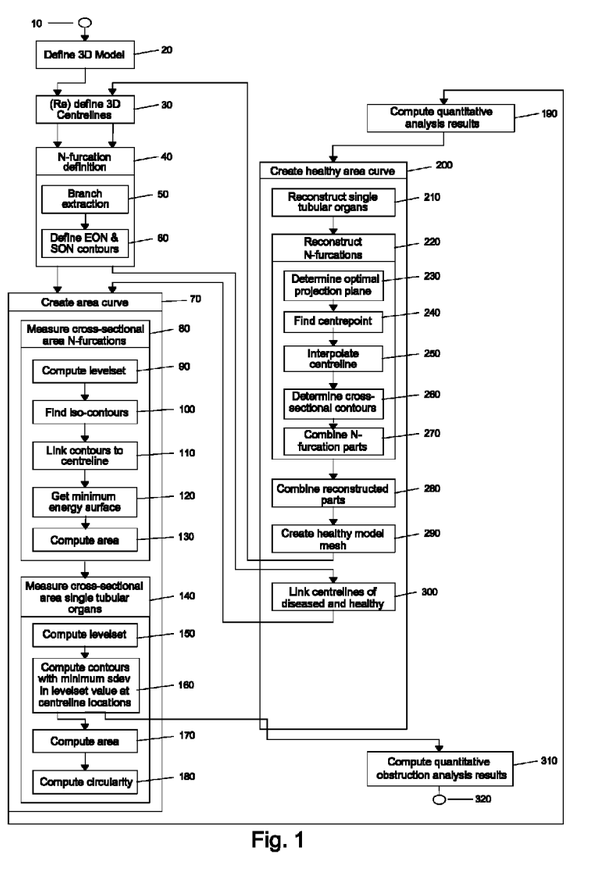
FIG. 1 is a flowchart of the invention's main steps in a preferred embodiment.

With reference to the block diagram of FIG. 1, an embodiment of the invention is now described.

Prior art teaches the definition of the 3D lumen wall of the vessels as represented by block 20 in FIG. 1. This is assumed to be a lumen wall surface mesh that is open at the in-flow and out-flow plane: In X-ray one can for example proceed as disclosed in cited document US2010/021025 by connecting separately reconstructed bifurcations models to form a 3D tree. As another example in MRA this can be achieved as in "Model-Based Segmentation Of Cardiac And Vascular Images", W J Niessen, proceedings of IEEE international symposium on biomedical imaging 2002, pp 22-25. Still another example, in ultrasound this can be achieved as in U.S. Pat. No. 6,251,072. Yet another example, in CTA this can be achieved as in "Robust CTA lumen segmentation of the atherosclerotic carotid artery bifurcation in a large patient population", Manniesing et al, Medical Image Analysis 14 (2010), pp. 759-769.

Given a 3D model of the lumen wall, a surface mesh of that model can be made (see for example William E. Lorensen, Harvey E. Cline: "Marching Cubes: A high resolution 3D surface construction algorithm". In: Computer Graphics, Vol. 21, Nr. 4, July 1987). Depending on the chosen approach, one might need to open the resulting mesh at the in-flow and out-flow planes.

Hereafter we define the 3D centrelines (see block 30 in FIG. 1). This is also done if a 3D centreline was already defined in step 1, as we want to ensure that centreline based results, such as length, over the arteries are measured the same independently from the underlying imaging modality. This is prior art (see for example "Robust and objective decomposition and mapping of bifurcating vessels", Antiga L, Steinman D A, IEEE transactions on medical imaging vol. 23, no 6, June 2004).

Within the tree, we now define parts where vessels split-up into N vessels (N>=2), called N-furcations, which are handled as single objects during the analysis, and parts that can be analysed as single vessel (see block 40 in FIG. 1), which is compatible with the methodology for 2D bifurcation analysis (see cited United States Patent Application published with number US2009/0060298).

First the tree branches are extracted (see block 50 in FIG. 1). This can be done, for example, according to the teachings of "Robust and objective decomposition and mapping of bifurcating vessels", Antiga L, Steinman D A, IEEE transactions on medical imaging vol. 23, n. 6, June 2004.

Figure 2:
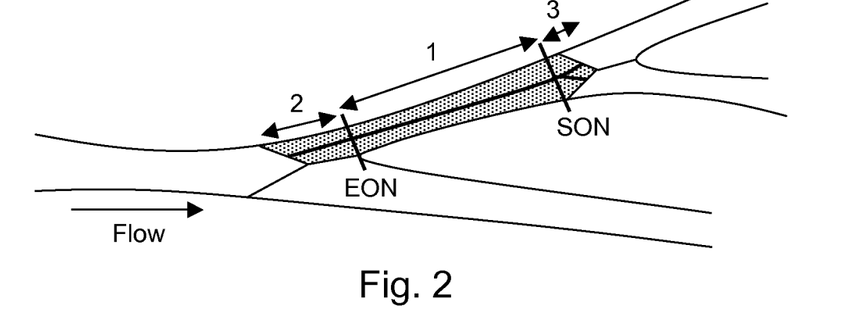
FIG. 2 is a schematic illustration of a branch containing N-furcation (N=2) and single vessel regions, including the boundaries of the regions depicted by EON and SON as well as the centrelines of the branch.
Figure 4:
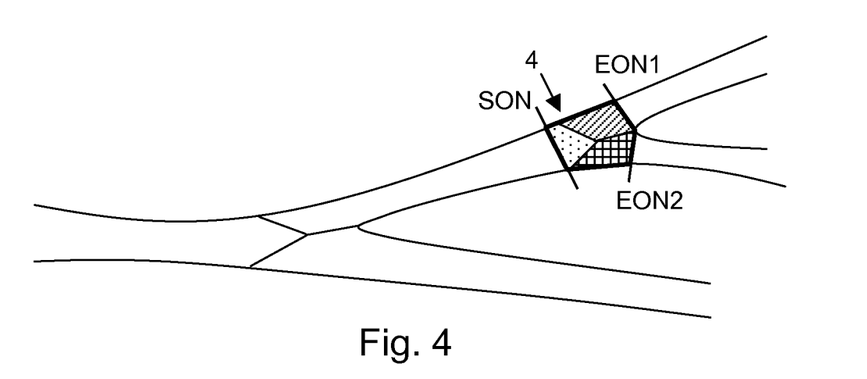
FIG. 4 is a schematic illustration of an N-furcation (N=2), constituted by a distal splitting region of a proximal branch (dotted area), and the proximal splitting regions of the branches directly distal to that proximal branch (dashed and grid-marked areas), where the splitting regions of the branches are depicted by SON, EON1 and EON2.

Within each branch, two region types may be present: single vessel and/or splitting regions (proximal and/or distal) as shown in FIG. 2. In this figure, branch single vessel region is indicated by reference number 1, while references 2 and 3 respectively identify proximal splitting region and distal splitting region. By definition the root branch of the tree does not contain a proximal splitting region, whereas leaf branches of the tree do not contain a distal splitting region. A branch without single vessel region can also occur. Each N-furcation in the tree consists of regions of N+1 branches; the distal splitting region of a branch, together with the proximal splitting regions of the N branches directly distal to it, form a single N-furcation 4 as shown in FIG. 4.

Figure 3:
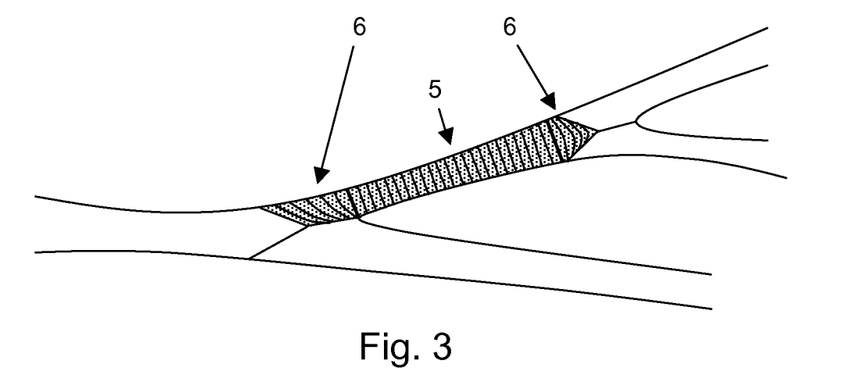
FIG. 3 is a schematic illustration of the two types of cross-section present in the branch.

In the region of each branch that can be analysed as single vessel, at each centreline location a straight intersecting surface 5, or cross-section, can be defined (elaborating on the cross-sectional measurement in conventional QCA analysis) whereas in the splitting regions of the branch surfaces between the lumen walls are defined which are not necessarily within a single plane (a measurement perpendicular to the local blood-flow, elaborating on the 2D bifurcation methodology's cross-sectional measurement). We will refer to the latter surfaces as curved cross-sections 6, whereas cross-sections in the single vessel regions are referred to as straight cross-sections (see FIG. 3).

This distinction between straight and curved cross-sections enables the identification of the single vessel region within each branch: we define the single vessel region as the part of the branch containing—an unbroken series of—straight cross-sections. The boundaries of the single vessel region are given by the most proximal and distal straight cross-sections of the branch, called End of N-furcation (EON) and Start of N-furcation (SON), respectively (FIG. 2). As a single vessel has a single centreline, the origins of the straight cross-sections can only be located on the centreline piece proximal to the centreline split-point within the branch (which we call the proximal centreline). Given the EON and SON, we know the proximal and distal splitting regions of the branch: the proximal splitting region is the region of the branch proximal to the EON and the distal splitting region the region of the branch distal to the SON.

The EON and SON need to be defined in order to conclude the N-furcation definition (see block 60 in FIG. 1). The SON of a branch is computed by finding the branch's most distal straight cross-section. This cross-section must be entirely part of the branch only, and may thus not be part of a neighbouring branch. The centreline location must lie within the plane. More specifically, the centreline location must lie within the cross-sectional contour. Furthermore, the cross-sectional plane's normal must be oriented such that both the cross-section has minimal surface area and the cross-section is perpendicular to the local vessel orientation. The latter is automatically true if measured far enough from the N-furcation. Therefore, as an initial location on the centreline, or centreline point, we compute the cross-section at the centreline location which is at a local radius proximal to the end of the proximal centreline of the branch. Here local radius is defined as the shortest distance from centreline point to lumen surface (which, in this case, is measured at the end of the proximal centreline). If a valid cross-section cannot be calculated, we take an initial location which is located more proximally. Once we have found a location for which a valid cross-section can be found, we try to find the minimal surface area cross-section. Next we move to a more distal location. The movement is only allowed in case the plane of the cross-section at the previous location defines a cross-section there that is entirely within the branch at the more distal centreline location. If the movement is allowed, the minimal surface area cross-section at the more distal centreline location is computed. This process is repeated until the distal movement is not possible anymore.

Hereafter a similar approach is used to define the branch's EON; we define an initial location distal to the start of the proximal centreline (i.e. the start of the branch) based on a local radius measured at the start of the proximal centreline and repeatedly try to find a minimal surface area cross-section more proximally.

The minimum surface area cross-section at a given centreline location o can be found by computing the plane through o with plane orientation such that the surface area of the branch-plane intersection with o in its interior is minimal, which is a minimization of a function: $Fo\{R,R\} \rightarrow \{R\}$. The domain of F is specified in sphere coordinates $\{phi, theta, r\}$, where r is the radius and can be omitted as we are only interested in the orientation of the cross-sectional plane. The range of F describes the (real) surface area. As the domain is cyclic (for both angles), we limit the domain to all angle combinations within the rectangle $\{[-PI,PI],[-PI,PI]\}$. The minimization problem is solved numerically by sampling F at a regular interval from its (limited) domain, which is split up in rectangular regions having width W and height H. For each W×H region, its centre is taken as sample point. Based on the areas computed using the orientation samples, we replace the domain of F by the region whose sample results in minimal surface area. The same steps are then performed based on the replaced domain. This process of replacing is repeated until the domain size reaches a threshold, making sure we do not suffer from numerical noise. Effectively, we are zooming in onto the correct result. In general, one has to be careful with such an approach, as it can result in zooming in onto a local minimum; F may have numerous local minima. However, there is a single minimum that stands out. Evaluating the function at some distance from its corresponding domain value still results in zooming in onto the correct (minimum) region, as long as the size of the region is sufficiently small (PI/8 suffices). The evaluation of the function F at a given orientation means computing the area of the intersection between the lumen wall and the plane with that orientation, which is trivial as it reduces to the problem of finding plane—mesh intersections. The individual intersections form one or more contours of which we discard the non-closed ones. Hereafter, only at most one contour will have the centreline position in its interior which is identified via the intersection number test. Checking if all line segments of that contour are part of the branch is trivial, as this information is known per (intersected) triangle of the 3D model. If there is no such contour or the check fails, F cannot be evaluated at this sample, and we ignore the corresponding region. Given the intersection contour, area computation is trivial as well, as the contour is located in a single plane, so the problem reduces to a 2D closed contour area computation.

Relevant clinical parameters are the cross-sectional area and diameter (see block 70 in FIG. 1). For the diameter, the diameter of a circle with the same area as the cross-section is taken.

Figure 5A:
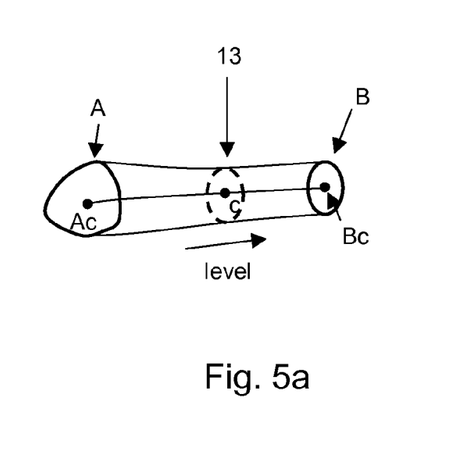
FIG. 5 is a schematic illustration of the elements necessary for the linking of centreline points to iso-contours in proximal (a) and distal (b) splitting regions, where for convenience the relation to the 2D image is given as well.

At the proximal splitting region of each branch, we proceed as follows (see block 80 in FIG. 1): we compute the levelset between the circumferential contour A bounding the branch at its proximal side, and that of the first straight cross-section B (see block 90 in FIG. 1) of the branch as computed above (FIG. 5a). The surface—centerline intersections Ac and Bc are then found. Computing the levelset between 2 contours of a mesh model is prior art, see for example "Nondistorting flattening maps and the 3-D visualization of colon CT images" published in IEEE Trans Med Imaging 2000 December; 19 (12):1267. Iso-contours describing mesh points with the same assigned level (iso-values) can be constructed (see block 100 in FIG. 1), which equal circumferential contours of the lumen wall. We link the iso-contours to our centreline of the branch (see block 110 in FIG. 1): first we will fit a minimum energy surface mesh through the contours A and B. The minimum energy surface is needed as we want to enable measurements perpendicular to the blood flow. The centreline location c is located on the centreline between Ac and Bc. The length over the centreline between c and Ac divided by the centreline length between Ac and Bc results in a fraction d. The iso-contour 13 with the iso-value which is at the same fraction d between the first and last level is linked to location c. The minimum energy surface mesh corresponding to location c is then computed, based on the points of the iso-contour. This mesh results in a curved cross-section. The corresponding area of this cross-section can then be computed by taking the sum of the areas of the mesh elements (see block 130 in FIG. 1).

Figure 6A:
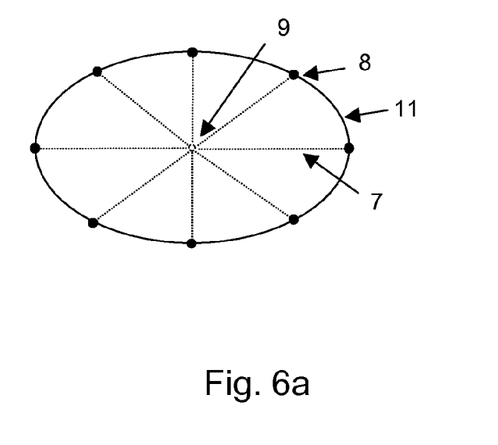
FIG. 6 is a schematic illustration of how the curved cross-section construction is done starting with the iso-contour, its points are used to define rays from the points to centre of gravity (a); the rays are then sampled by inner rings (b)
Figure 6B:
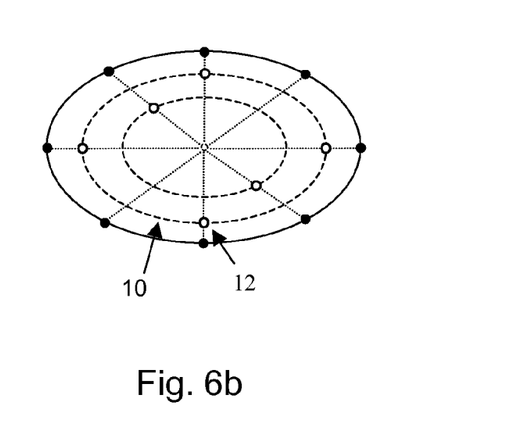

For the derivation of the minimal energy surface mesh of a circumferential contour (see block 120 in FIG. 1), an iterative approach is chosen: we first create rays 7 (straight lines) from each contour vertex 8 to the centre of gravity 9 (see FIG. 6a) and then sample these rays 7 to form n rings 10 (see FIG. 6b). The first ring is the contour 11 itself and its number of samples therefore equals the amount of contour points 8. Every inner ring 10 has half the amount of samples 12 of its surrounding ring (rounded upwards). The lowest ring has either 2 or 3 samples. Ring i samples rays $\{1,1+2^{\wedge}(i-1), \ldots, 1+(m-1)*2^{\wedge}(i-1)\}$ where m is the amount of samples in ring i. A mesh can now be constructed by forming a triangulation based on inner-connection of all the samples first with their neighbours within the same ring and then between adjacent rings. Each sample can now be moved with the average of all vectors to its neighbours. Note however that the samples of ring 1 remain fixed. We can stop moving when the change in total area and/or maximum node motion reach a certain significance threshold.

Figure 5B:
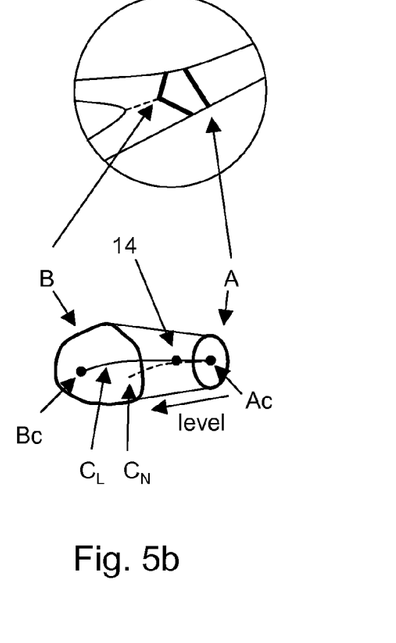

A similar approach is followed at the distal side of each branch, but then the levelset between the contour A, the contour of the last straight cross-section of the branch and the circumferential contour B bounding the branch at its distal side is computed (see FIG. 5b). As we have multiple centrelines in the distal splitting region (see FIG. 2), we pick the longest centreline route CL between A and B. Note that a route may include common centreline pieces between SON and a centreline split-point 14. The linking of this longest route is then similar to linking within the proximal splitting region. Linking the remaining centrelines is now only necessary for the centreline pieces present after a split-point. For every c on the piece of CL after a split-point (CL'), we divide its length to the split-point by the length of CL' to get fraction d'. Next we look at the same fraction d' of the length between the split-off and the end of centreline CN, which is the second longest route, and couple the corresponding centreline location of CN to the iso-contour to which c is linked. This is repeated until all locations on centrelines in the distal splitting region are coupled to an iso-contour. Computation of the curved cross-sections is done as described above for the proximal splitting region.

Figure 7A:
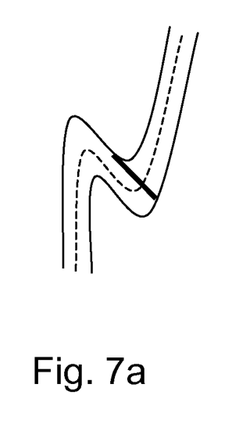
FIG. 7 is a schematic illustration that depicts the definition of a cross-section perpendicular to the centreline (a) and using the method according to the invention (b) at a given centreline location.
Figure 7B:
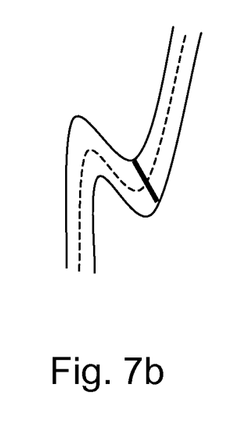
Figure 8A:
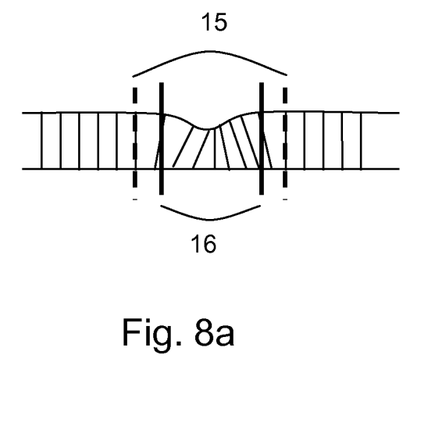
FIG. 8 is a schematic illustration that depicts differences in cross-sectional contour definitions based on minimizing area resulting in overestimation of the obstruction extent (a) versus standard deviation in level-set value (b)
Figure 8B:
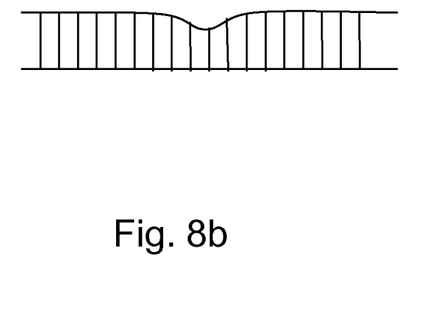

For the single vessel region of each branch, we proceed as follows (see block 140 in FIG. 1). We do not define cross-sections perpendicular to the centreline, as this results in a cross-sectional area overestimation in case of non-constant tubular organ curvature (see FIG. 7). Another significant problem with defining cross-sections perpendicular to the centreline is the fact that the cross-sections bend towards obstructions and as of such overestimation of the obstruction extent is likely to occur (see FIG. 8a). In this figure, reference numbers 15 and 16 respectively indicate the overestimated and the actual obstruction extent. This problem cannot be solved when the already described method for area minimization is used to define the cross-sections in between the single vessel region boundaries. Therefore, as part of the invention, we propose the following method: similar to determining the levelset between the proximal branch boundary and the contour of the EON cross-section as described for the proximal splitting region, we compute the levelset between the cross-sectional contours of EON and SON of the branch (see block 150 in FIG. 1). Hereafter we apply the same cross-sectional area minimization method introduced in step 3 for each centreline position in the single vessel region. However, instead of the area, the range of the function now describes standard deviation in levelset value of the set of intersection points with the lumen wall for a given orientation (see block 160 in FIG. 1). This results in straight cross-sections which do not suffer from the problems described previously (see FIG. 7b and FIG. 8b). Hereafter, the cross-sectional area computation is trivial as its bounding contour is located in a single plane, so the problem reduces to a 2D closed contour area computation (see block 170 in FIG. 1). This method is particularly advantageous and can be applied in general, i.e. not necessarily in the framework of the present invention, for determining cross-sections of tubular organs between a proximal and a distal boundary surface.

Now that the centrelines and area graphs are derived, quantitative analysis results can be computed (see block 190 in FIG. 1). Such results include, but are not necessarily limited to, lengths, volumes, angles between branches, derived diameters (i.e. diameters of circular cross-sections having the same area as the computed cross-sectional areas), and curvature. During the centreline extraction maximum inscribed spheres were found. Based on the straight cross-sections, minimum bounding circles can be defined at each centreline position in a single vessel region. The circularity graph over the tree (only the single vessel regions) indicating its state of healthiness at each position can then be found by dividing the radius of the inscribed sphere by the radius of the bounding circle at the centreline positions (see block 180 in FIG. 1).

Block 200 in FIG. 1 exemplifies the further steps that can be performed for computations of healthy area and diameter of the vascular tree in 3D. The healthy area function can be derived from the healthy diameter function: area=$0.25*PI*diameter^2$. As a further aspect of the invention, we define a method to derive the healthy diameters of the vascular tree that is fully 3D, which is stable in the sense that healthy diameter measurements within N-furcations can be consistently linked to the diseased diameters, which may be used for reference diameter or reference area based quantitative analysis. In order to determine the healthy diameters, a 3D model of the healthy tree is made, which is helpful for visual interpretation, as displaying of the plaque is in conventional QCA analysis. The healthy tree reconstruction algorithm generates a model of how obstructed parts or dilated parts of the tree would look like if they had been healthy. An example of an obstructed bifurcation model and the corresponding healthy model is given in FIG. 11a and FIG. 11b, respectively.

The healthy 3D model is determined for example with the following sub-steps:

1) A 3D contour model (i.e. centrelines and cross-sectional contours per centreline position describing the (healthy) lumen) is made of each of the single tubular organs (see block 210 in FIG. 1): We create the 3D obstruction borders and diameter reference curves for the tree (both can be computed automatically if not user-defined) and from this the 3D healthy model of each single tubular organ. This is prior art and can be achieved for example via a subset of the methods described in cited document U.S. 2010/021025.

Figure 9:
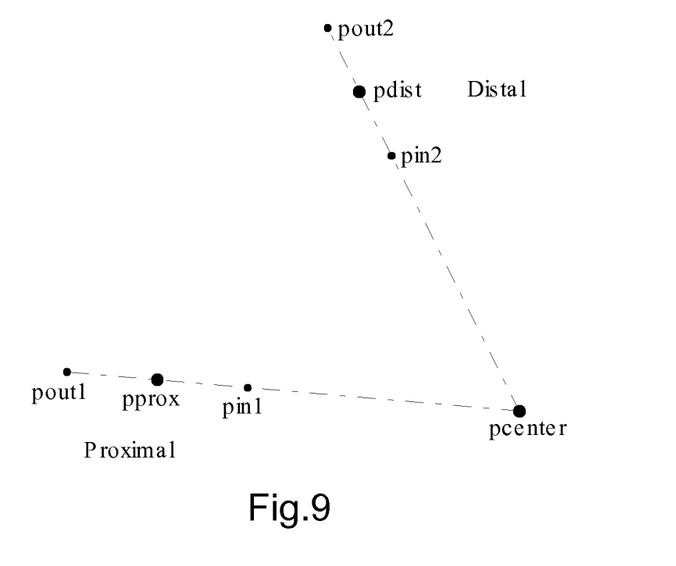
FIG. 9 schematically illustrates the principle of N-furcation reconstruction: pprox and pdist are the last respectively first centerpoint of the proximal and one of the distal single tubular organs at a given N-furcation. Rotating a plane around the line between pprox, pdist gives intersections pin1, pout1 of the circular cross-section at pprox and pin2, pout2 of the circular cross-section at pdist. The lines pin1-pout1, pin2-pout2 intersect at pcenter.

2) The generation of the healthy splitting region(s) is an important step to derive the healthy diameter curves for the N-furcation(s) (see block 220 in FIG. 1). This is accomplished per N-furcation involved by fitting a model that minimizes the curvature of the lumen wall from proximal to distal branches, thus presenting a model in which the flow behaves as if there was no obstruction within the N-furcation. The N-furcation is divided into N parts, each getting a separate healthy reconstruction (see in FIG. 9) and describing the distal splitting region of a proximal branch and the proximal splitting region of one of the branches directly distal to it. For each part we use the most distal contour PC of the proximal single tubular organ's healthy vessel and its corresponding centreline location pprox. We also use the first contour of the i-th distal single tubular organ's healthy vessel and its corresponding centreline location pdist for the i-th part. Details are explained in sub-steps 2a-2d:

2a. An optimal projection plane is determined in which centreline reconstruction will be performed (see block 230 in FIG. 1): a plane is rotated around the line between pprox and pdist. For every angle, the intersection points of the plane with PC and DC are calculated. This should result in 2 intersection point pairs, (pin1, pout1) of PC, (pin2, pout2) of DC ordered such that |pin1−pin2| is minimal (see FIG. 9). If no 4 points are found, the plane is ignored. The plane with minimal |pin1−pin2| distance is the optimal projection plane.

2b. The centre point pcenter is found as the intersection point of the line through pin1 and pout1, and the line through pin2 and pout2 (see block 240 in FIG. 1).

Figure 10:
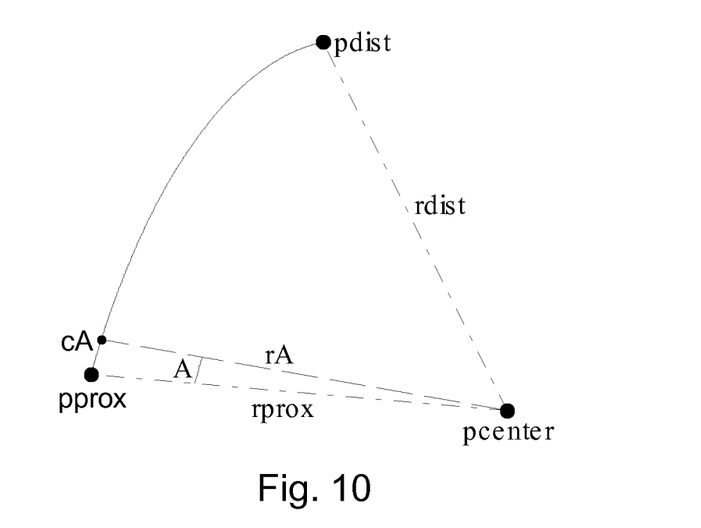
FIG. 10 is a schematic illustration of the healthy centreline reconstruction. The centreline point cA on the arc between pprox (with distance rprox to pcenter) and pdist (with distance rdist to pcenter) has a distance rA to pcenter for given angle A.
Figure 11A:
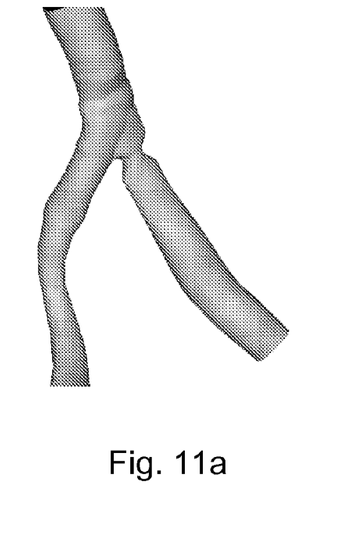
FIG. 11 is a series of screenshots where (a) shows a model of an obstructed vascular tree, (b) shows the healthy model of an obstructed region of that vascular tree between defined obstruction borders as light grey overlay, (c) shows the diameter graphs from proximal branch start to the main distal branch end, and (d) from the proximal branch start to the side distal branch end. In (c) and (d) diseased and healthy diameters are indicated in black and grey, respectively. The striped lines indicate the obstruction region boundaries and dotted line the position of relatively largest stenosis (note that this value was found in the distal part of the main branch of (c) and therefore no such line is present in (d)).
Figure 11B:
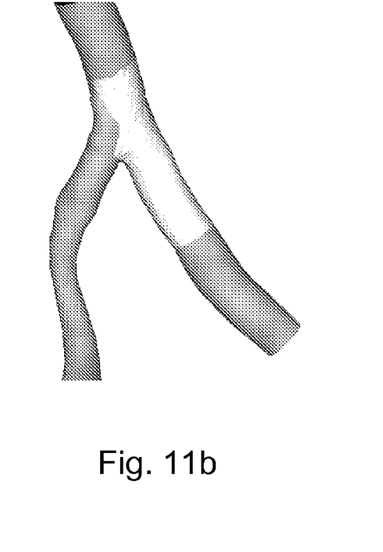
Figure 11C:
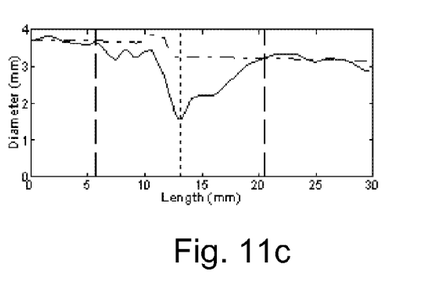
Figure 11D:
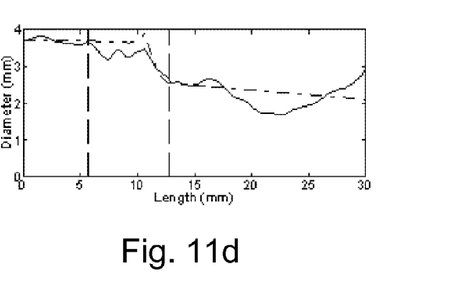

2c. The 3D centreline is generated between pprox, pdist: as a function of an angle A, where A is limited to all real angles between vectors pprox-pcenter and pdist-pcenter with vector lengths rprox and rdist, we define the centreline position cA at distance rA from pcenter where rA is linearly interpolated between rprox, rdist based upon angle A (see FIG. 10, block 250 in FIG. 1)

2d. For each centreline location cA the cross-sectional contour is the circle with center cA, diameter as linearly interpolated between the diameter at pprox, pdist according to A and normal equal to the local centreline direction (see block 260 in FIG. 1).

Combining 2c, 2d gives a contour model as in step 1 for part i of the N-furcation.

The contour models of all parts of the N-furcation can then be combined to form the contour model of the N-furcation (see block 270 in FIG. 1).

3) The contour models for all parts from step 1 and 2 are combined together to form a contour model of the healthy tree (see block 280 in FIG. 1): as all parts are of the same type and have known topological order, this is straightforward.

4) The contour model is transformed into a healthy lumen surface mesh model (see block 290 in FIG. 1). For example, a triangulation between each two successive contours can be made. When these are combined, a description of the surface of the model can be obtained when looking from the outside, which, in turn can then be used to find a lumen surface mesh model using prior art. For example, this can be done using a marching cubes algorithm, which is extensively described in literature as explained earlier.

Once defined the 3D healthy model, the further steps can be the same as those for the original 3D model. This is exemplified in FIG. 1 by the link between blocks 290 and 30. Of course also different steps can be performed.

5) In the healthy model we can redefine the centrelines (see block 30 in FIG. 1), define the branches (see block 50 in FIG. 1), and define the first and last straight cross-section of each branch (see block 60 in FIG. 1).

6) For analysis purposes, the centrelines of the healthy model are sampled such that there is a one-to-one linking connection to the original centreline locations at which cross-sections are defined (see block 300 in FIG. 1). By means of this one-to-one link, we can also define a corresponding link between all related analysis results (for example healthy and diseased cross-sectional area, diameter). The linking is done per branch, since both models have the same topology and thus contain equivalent branches.

7) The healthy area (and diameter) at each healthy centreline sample from step 6 is determined: we define the cross-sections within the single vessel (see blocks 140, 150, and 160 in FIG. 1) and splitting regions (see blocks 70, 80, 90, 100, 110, 120, and 130 in FIG. 1), all as described earlier in this invention. Since the input reference curve information is leading outside the splitting regions, area computation for the healthy single vessel regions is omitted (block 170 in FIG. 1), as this reference curve follows from the reconstruction of the single tubular organs (see block 210 in FIG. 1). Note however that contour computation (and thus levelset computation) is necessary for computing analysis results (see block 310 in FIG. 1). Also, as the healthy single tubular organ has circular cross-sections, computing circularity (block 180 in FIG. 1) is needless. Inside the splitting regions, the area and diameter from the healthy reconstructed cross-sections is used (see FIGS. 11c and 11d).

As part of the invention it is possible to ignore one or more distal branches when these are not of interest. Depending on the remaining number of distal branches, either an M-furcation (where 2<=M<N) remains or a single tubular organ. In all cases this means that in steps 1-7 we treat this as if the branch was not present at all. More importantly, when M=1: the involved input reference line is assumed to be the reference line of the single tubular organ that remains.

The last step consists of determining quantitative (obstruction) analysis results (see block 310 in FIG. 1) (for example by using the computed healthy and original 3D diameters as is also described for a 2D bifurcation analysis in the cited U.S. application published with number US2009/0060298). Such results are amongst others: diameter stenosis, obstruction percentage, plaque volume, volume stenosis, obstruction extent (obstruction borders), and position of largest obstruction (i.e. lesion position).

The invention claimed is:

1. Method for quantitative analysis of a tree or part of a tree formed by recursively splitting tubular organs, the method comprising:

providing a 3D model of said tree or part of said tree, said 3D model giving a representation of a surface of a lumen wall of the tubular organs forming the tree or part of the tree;

defining 3D centerlines of said tree or part of the tree;

identifying branches of the tree or part of the tree;

dividing each branch into one or more regions, said regions being of two different types including a single vessel region type and a splitting region type, wherein said splitting regions exist at a part of a branch selected from the group consisting of the proximal side of said branch and the distal side of said branch, wherein said single vessel regions and said splitting regions are defined by cross-section surfaces that intersect the 3D centerlines, and wherein said cross-section surfaces are determined by computing surface areas of cross-sections that intersect a number of locations of the 3D centerlines; and identifying N-furcations of the tree or part of the tree, each N-furcation being a part of the tree where a proximal tubular organ branches into N distal tubular organs with N≥2, wherein each N-furcation comprises the distal splitting region of a branch and the proximal splitting regions of the N branches directly distal to said branch.

2. Method according to claim 1, wherein:

boundary surfaces between a splitting region and adjacent single vessel regions are defined for each branch, said boundary surfaces including the cross-section surfaces of the adjacent single vessel regions.

3. Method according to claim 1, wherein:

the cross-section surfaces of the splitting regions are curved surfaces; and the cross-section surfaces of the single vessel regions are planar surfaces.

4. Method according to claim 3, wherein:

the cross-section surfaces of the splitting regions are curved in order to take into account perpendicularity to the flow of a fluid perfusing the tree or part of the tree in each of the splitting directions.

5. Method according to claim 3, wherein:

the planar surfaces of the single vessel regions each belong to a cut plane, perpendicular to a local branch orientation.

6. Method according to claim 3, wherein:

the proximal boundary surface of a single vessel region of a branch is computed by iteratively finding the most proximal planar cross-section surface over the 3D centerline of said branch, whose contour is entirely part of said branch, falls within a single plane containing the corresponding position on said 3D centerline and is oriented such that it has minimal area at said position; and the distal boundary surface of a single vessel region of a branch is computed by iteratively finding the most distal planar cross-section surface over the 3D centerline of said branch, whose contour is entirely part of said branch, falls within a single plane containing the corresponding position on said 3D centerline and is oriented such that it has minimal area at said position.

7. Method according to claim 6, wherein:

finding the orientation of said cross-section surface such that the area of said cross-section surface is minimal is computed by:

defining the orientation in a spherical domain, thereby ignoring the radius dimension;

limiting said domain to one cycle in each of both remaining angular dimensions;

splitting up said domain in rectangular subdomains and for each subdomain calculating the cross-sectional area for the orientation specified by the centervalue of said subdomain;

replacing said domain by one of said subdomains, more specifically the subdomain for which the calculation of said cross-sectional area for said centervalue resulted in minimal area; and repeating calculation of said centervalue and replacing of said subdomain until the domain size reaches a pre-defined threshold.

8. Method according to claim 3, wherein:

for proximal splitting regions, the area of the curved cross-section surfaces is calculated by:

computing the levelset between the circumferential contour bounding the branch at its proximal side and the contour surrounding the distal boundary surface to determine corresponding iso-contours which circumferentially contour the lumen;

linking the iso-contours to 3D centerline points based on the iso-value that corresponds to the 3D centerline point located at the distance where the fraction of the total centerline distance between the first and last iso-contours equals the iso-value having same fraction between the levels of said first and last iso-contours;

computing for each 3D centerline point the surface of the cross-section bounded by the linked iso-contour of said 3D centerline point, said surface being curved and having the minimum energy; and computing the area of said surface for each said 3D centerline points.

9. Method according to claim 8, wherein:

for distal splitting regions, the area of the curved cross-section surfaces is calculated by:

computing the levelset between the contour surrounding the proximal boundary surface and the circumferential contour bounding the branch at its distal side;

linking the iso-contours to 3D centerline points of the 3D centerline having the longest route between said contours based on the iso-value that corresponds to the 3D centerline point located at the distance where the fraction of the total centerline distance between the first and last iso-contours equals the iso-value having same fraction between the levels of said first and last iso-contours;

linking the iso-contours to centerline points of the remaining 3D centerlines after a centerline split-off point using already present links, based on the fraction of the distance of a 3D centerline point to said split-off point compared to the total distance measured between the split-off of 3D centerlines to the end of the branch, where a said already present link has an equal fraction of distance between said split-off and the end of the branch;

computing for each 3D centerline point the surface of the cross-section bounded by the linked iso-contour of said 3D centerline point, said surface being curved and having the minimum energy; and computing the area of said surface for each said 3D centerline point.

10. Method according to claim 3, wherein:

for single vessel regions, the area of the planar cross-section surfaces is calculated by:

computing the levelset between the contour surrounding the proximal boundary surface and the contour surrounding the distal boundary surface;

linking each 3D centerline point to cross-sectional contours having minimum standard deviation in levelset value whereby said contours surround a planar cross-section containing said 3D centerline point; and computing the area of said planar cross-section for each said 3D centerline point.

11. Method according to claim 9, wherein:

the minimal energy surface of a circumferential contour within a splitting region is calculated iteratively by:

defining straight lines from each contour vertex of said circumferential contour to the center of gravity of said circumferential contour and dividing said lines in n rings containing m samples wherein the vertices of said circumferential contour are the samples of the first ring and each inner ring contains less samples than its outer neighbour and, besides the first two, two successive rings do not sample same rays;

defining a surface mesh between ring points;

computing total area of said surface mesh;

fixing said samples of said first ring and moving each other sample in a mean neighbor direction until change in at least one of mesh area and movement of the samples is less than a corresponding predefined threshold.

12. Method according to claim 1, wherein:
quantitative analysis results are presented with reference to the tree, said results including length, area, diameter, angles between branches, and curvature.

13. Method according to claim 1, further comprising:
determining a circularity graph indicating healthiness over the tubular organ, the circularity graph derived by dividing the radius of a maximum inscribed sphere by the radius of the minimum bounding circle of a cross-section at each 3D centerline position within a single vessel region.

14. Method according to claim 1, wherein:
a healthy reconstruction is provided, said healthy reconstruction being a healthy 3D model giving a representation of the surface of the healthy lumen wall of the tubular organs forming the tree or part of the tree.

15. Method according to claim 14, further comprising:
creating healthy reconstructions of the singular tubular organs forming the tree or part of the tree;
creating healthy reconstructions of the N-furcations forming the tree or part of the tree, each of said healthy reconstructions of the N-furcations being divided in N parts each describing minimum lumen curvature;
combining all healthy reconstructions of the singular tubular organs and N-furcations into one contour model;
creating a healthy model surface mesh from said contour model forming the healthy tubular organs forming the tree or part of the tree;
defining 3D centerlines for the healthy tubular organs forming the tree or part of the tree;
defining N-furcations in the healthy tubular organs forming the tree or part of the tree;
linking centerlines for the healthy tubular organs forming the tree or part of the tree to the other centerlines of the tree or part of the tree;
creating cross-sections and computing area curves for N-furcations in the healthy tubular organs forming the tree or part of the tree;
creating cross-sections and computing area curves for single tubular organs in the healthy tubular organs forming the tree or part of the tree;
wherein the cross-sections and area curves for N-furcations and the single tubular organs in the healthy tubular organs forming the tree or part of the tree are derived by identifying branches in the healthy tubular organs forming the tree or part of the tree and by dividing each branch in one or more regions, said regions being of two different types including a single vessel region type and a splitting region type, wherein said splitting regions exist at a part of a branch selected from the group consisting of the proximal side of a branch and the distal side of said branch, and wherein different cross-section surfaces are defined in said regions.

16. Method according to claim 15, wherein:
the linking of the centerlines is based on the healthy model surface mesh having the same topology as the tree.

17. Method according to claim 14, wherein:
quantitative analysis results are presented with reference to the healthy tree reconstruction in relation to the tree reconstruction.

18. Method according to claim 14, wherein:
splitting regions of the healthy tubular organs forming the tree or part of the tree are reconstructed with a model that minimizes the curvature of the lumen wall going from the start of an N-furcation to each of the distal ends of that N-furcation.

19. Method according to any claim 14, wherein:
said healthy 3D model is assumed healthy except for one or more obstructed parts of said healthy 3D model, whereby each of said obstructed parts reflects a 3D model of a subtree of said tree and said obstructed parts are automatically derived based upon one or more automatically computed or user supplied lesion positions.

20. Method according to claim 14, wherein:
said healthy 3D model is used to provide visual feedback of the plaque shape and location.

21. Method according to claim 1, wherein:
one or more subtrees of tubular organs originating from any of the N-furcations of said tree are ignored.

22. A computer product directly loadable into the memory of a computer and comprising non-transitory software code portions executable on the computer for performing the method of claim 1.

23. Apparatus for quantitative analysis of a tree or part of a tree of recursively splitting tubular organs, the apparatus comprising means for generating a 3D model of said tree or part of said tree, such 3D model giving a representation of the surface of the lumen wall of the tubular organs forming the tree or part of the tree, and processing means programmed for performing the method according to claim 1.

24. Method according to claim 1, wherein:
the 3D model is derived from a plurality of 2D images; and
each branch is divided into one or more regions based on the 3D model and independent of the image data of said plurality of 2D images.

25. Method for quantitative analysis of a tree or part of a tree formed by recursively splitting tubular organs, the method comprising:
providing a 3D model of said tree or part of said tree, said 3D model giving a representation of a surface of a lumen wall of the tubular organs forming the tree or part of the tree;
defining 3D centerlines of said tree or part of the tree;
identifying branches of the tree or part of the tree;
dividing each branch into one or more regions, said regions being of two different types including a single vessel region type and a splitting region type, wherein said splitting regions exist at a part of a branch selected from the group consisting of the proximal side of said branch and the distal side of said branch, and wherein different cross-section surfaces are defined in said regions;
determining the cross-sectional area at a number of positions of a given centerline by computing the area of the cross-section surfaces as defined for single vessel regions and for splitting regions; and
identifying N-furcations of the tree or part of the tree, each N-furcation being a part of the tree where a proximal tubular organ branches into N distal tubular organs with $N \geq 2$, wherein each N-furcation comprises the distal splitting region of a branch and the proximal splitting regions of the N branches directly distal to said branch;
wherein the cross-section surfaces of the splitting regions are curved surfaces, and the cross-section surfaces of the single vessel regions are planar surfaces.

* * * * *